(12) United States Patent
Guglielmotti et al.

(10) Patent No.: US 6,191,158 B1
(45) Date of Patent: Feb. 20, 2001

(54) PHARMACEUTICAL COMPOSITION ACTIVE IN REDUCING PRODUCTION OF MCP-1 PROTEIN

(75) Inventors: Angelo Guglielmotti; Claudio Milanese, both of Rome (IT)

(73) Assignee: Aziende Chimiche Riunite Angelini Francesco A.C.R.A.F. S.p.A., Rome (IT)

( * ) Notice: Under 35 U.S.C. 154(b), the term of this patent shall be extended for 0 days.

(21) Appl. No.: 09/463,665

(22) PCT Filed: Jul. 22, 1998

(86) PCT No.: PCT/EP98/04925

§ 371 Date: Apr. 25, 2000

§ 102(e) Date: Apr. 25, 2000

(87) PCT Pub. No.: WO99/04791

PCT Pub. Date: Feb. 4, 1999

(30) Foreign Application Priority Data

Jul. 28, 1997 (IT) .............................................. MI97A1788

(51) Int. Cl.⁷ ................................................... A01N 43/56
(52) U.S. Cl. .............................................................. 514/405
(58) Field of Search ............................................... 514/405

(56) References Cited

U.S. PATENT DOCUMENTS 3,970,194 * 7/1976 Palazzo ................................ 514/405
4,352,813 * 10/1982 Silvestrini et al. ................... 514/405
4,551,477 * 11/1985 Silvestrini et al. ................... 514/405

OTHER PUBLICATIONS

1996.*
Van Wauwe et al, Inflamm. Res., vol. 45, #7, pp. 357–63, 1996.*

* cited by examiner

*Primary Examiner*—James H. Reamer
(74) *Attorney, Agent, or Firm*—Oblon, Spivak, McClelland, Maier & Neustadt, P.C.

(57) ABSTRACT

Use of a compound having formula (I) and salts thereof with pharmaceutically acceptable organic or inorganic bases, for preparing a pharmaceutical composition active in the treatment of disorders characterized by production of MCP-1 protein.

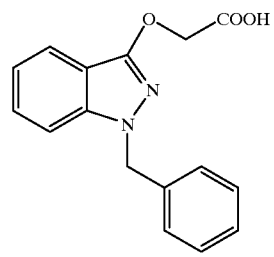

(I)

4 Claims, No Drawings

PHARMACEUTICAL COMPOSITION ACTIVE IN REDUCING PRODUCTION OF MCP-1 PROTEIN

The present invention relates to the use of indazol oxyalkanoic acids for preparing a pharmaceutical composition active in the treatment of disorders characterized by production of MCP-1 protein.

U.S. Pat. No. 3,470,194 describes (1-benzyl-1H-indazol-3-yl)-oxyacetic acid of formula

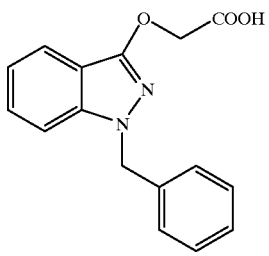

(I)

endowed with anti-inflammatory activity and also known as bendazac.

Moreover, the use of bendazac and salts thereof, with pharmaceutically acceptable bases, is known in therapy of some dyslipemia (U.S. Pat. No. 4,352,813), pigmental retinitis (EP-B-131 317) and cataract (U.S. Pat. No. 4,451, 477).

Furthermore, the use of bendazac and salts thereof was disclosed for preventing opacification of contact lenses (EP 255 967).

It has now been found that the compound having the formula (I) is also active in reducing production of MCP-1 protein.

As already known, MCP-1 protein (Monocyte Chemotactic Protein-1) is a chemokine belonging to the β subfamily of the chemokines. It possesses a strong chemotactic activity for monocytes and also acts on T lymphocytes, mastocytes and basophils.

Other chemokines belonging to the β subfamily are, for example, MCP-2 (Monocyte Chemotactic Protein-2), MCP-3, MCP-4, MIP-1α and MIP-1β, RANTES and protein 1309.

The β subfamily differs in structure from the α subfamily; in fact, whilst the first two cysteines of the chemokines of the a subfamily are separated by an interposed amino acid, the first two cysteines of the β subfamily are adjacent to each other. MCP-1 is produced by several types of cells (leucocytes, platelets, fibroblasts, endothelial cells).

Of all the known chemokines, MCP-1 shows the highest specificity in respect of monocytes and macrophages, for which it is not only an attracting factor but also a stimulus of activation, thus inducing a process of production of superoxides and arachidonic acid, as well as being a stimulus of amplification of phagocytic activity.

Secretion of chemokines in general and especially of MCP-1 is typically induced by numerous factors such as, for example, interleukin-1 (IL-1), interleukin-2 (IL-2), TNFα (Tumor Necrosis Factor α), γ-interferon and bacterial lipopolysaccharide (LPS).

In the human, MCP-1 has been found in a large number of diseases with acute or chronic course not classified in homogeneous categories by traditional medicine: for example, interstitial lung disorders (ILD), vasculitis and atherosclerosis and renal disorders such as, for example, nephrites, nephritic syndromes, nephrosis characterized by progressive, prolific, membranous or membranousprolific glomerulenephrite.

In interstitial lung disorders, MCP-1 released by pulmonary endothelial cells, attracts and activates competent cells with consequent release of mediators which damage the alveolar structures of the lung.

In vasculitis, MCP-1 is released by the endothelial cells of the vasa following harmful stimuli and attracts and activates monocytes and other cell types which become responsible for damage to the vascular wall.

In atherosclerosis, MCP-1 is produced by the vascular endothelium following damage to the vascular smooth muscle cells. MCP-1 attracts monocytes which initially adhere to the arterial wall and then migrate through the walls, contributing to formation of atheroma by stimulating proliferation of smooth muscle cells.

In renal disorders, phatogenetic mechanisms are characterized by activation of humoral and cellular factors that contribute in the onset of damages charged to glomerule and tubule. In particular, the initial event is almost always characterized by gut infiltration by white type cells. Such phenomenon is primed and monitored by soluble factors among whom MCP-1 that, due to its characteristics of chemotactic protein endowed with high specificity in respect of monocytes and macrophages, plays an essential part in this disorders.

The therapies currently used in these disorders, because they act upstream of the pathological phenomena, are aspecific and very often have numerous and at times serious side effects.

The above-mentioned therapies, moreover, only enable temporary remission of the pathological phenomena to be obtained and their high toxicity prevents their use for prolonged periods of the kind necessary on the other hand in diseases of chronic type.

For atherosclerosis, in particular, the drugs currently used only act on certain factors which contribute to formation of the atheroma, such as hypercholesterolaemia or hypertension, whilst having no effect on the target of the pathological process, i.e. the vascular wall.

Chemotactic factors in general and MCP-1 in particular are also very important in cases where complications occur following surgical interventions such as, for example, angioplasty, atherectomy, circulatory recovery techniques, transplants, organ replacements, tissue replacements and prosthetic implants. Onset of such complications often makes it necessary for the patient to undergo further intensive therapies or even a new intervention.

U.S. Pat. No. 5,571,713 claims a composition comprising an MCP-1 antisense oligonucleotide for in vitro inhibition of production of MCP-1 by mononuclear human cells and smooth muscle.

There is therefore still a strong need for a pharmaceutical composition which is effective in the treatment of disorders characterized by production of MCP-1, e.g. atherosclerosis, vasculitis, interstitial lung disorders, renal disorders, post-operative complications of cardiovascular surgery, in transplants or organ or tissue replacements and in prosthetic implants.

It is therefore an object of the present invention to provide an use of (1-benzyl-1H-indazol-3-yl)-oxyacetic acid (bendazac) of formula

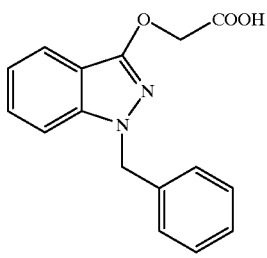

and salts thereof with pharmaceutically acceptable organic or inorganic bases,
for preparing a pharmaceutical composition active in the treatment of disorders characterized by production of MCP-1 protein.

Typical examples of disorders characterized by production of MCP-1 protein are: atherosclerosis, vasculitis, interstitial lung disorders, renal disorders, postoperative complications in cardiovascular surgery, in transplants or organ or tissue replacements and in prosthetic implants.

Preferably the pharmaceutical compositions according to the present invention are prepared in suitable dosage forms comprising an effective dose of at least one compound having the formula (I) or a salt thereof with a pharmaceutically acceptable base and at least one pharmaceutically acceptable inert ingredient.

Examples of suitable dosage forms are tablets, capsules, coated tablets, granules, solutions and syrups for oral administration; medicated plaster patches for transdermal administration; suppositories for rectal administration and sterile solutions for administration by the injectable, aerosol or ophthalmic routes.

Further suitable dosage forms are slow release and liposome based forms, for either the oral or the injectable routes.

The dosage forms may also contain other conventional ingredients, for example: stabilising preservatives, surfactants, buffers, salts for regulation of osmotic pressure, emulsifiers, sweeteners, coloring agents, flavourings, and the like.

If required by particular therapies, the pharmaceutical composition according to the present invention may contain other pharmacologically active ingredients whose concomitant administration is therapeutically useful.

The amount of compound having the formula (I) or of a salt thereof with a pharmaceutically acceptable base in the pharmaceutical composition according to the present invention may vary within a wide range depending on known factors such as, for example, the type of disease to be treated, the severity of the disease, the patient's body weight, the dosage form, the chosen administration route, the number of daily administrations and the efficacy of the selected compound having the formula (I). The optimum amount can nevertheless easily and routinely be determined by a person skilled in the art.

Typically, the amount of compound having the formula (I) or of a salt thereof with a pharmaceutically acceptable base in the pharmaceutical composition according to the present invention will be such that it ensures an administration level of from 1 to 100 mg/kg/day. Preferably the administration level is of from 5 to 50 mg/kg/day or still more preferably of from 2 to 20 mg/kg/day.

The dosage forms of the pharmaceutical composition according to the present invention may be prepared according to techniques which are known to the pharmaceutical chemist, comprising mixing, granulation, compression, dissolution, sterilization and the like.

The activity of the composition according to the present invention may be evaluated by the following Tests.

TEST I

Effect of Drug on Production of MCP-1

The capability of drug to reduce production of MCP-1 by leucocytes (PBMC) stimulated by LPS was evaluated. White blood cells were isolated by centrifugation on a Ficoll gradient and then stimulated with LPS in the presence or absence of scalar concentrations of drug under evaluation. The supernatant fluid was collected at the end and levels of MCP-1 were measured by means of a specific immunoenzymatic test.

TEST II

Effect of Drug on Cell Attraction in the Mouse "Air Pouch"

The action of drug was studied in an experimental model in the mouse, the said model being characterized by production of MCP-1, cell infiltration and formation of exudate. Mice were fed ad libitum with a standard diet for rodents or with the same diet with addition of drug under evaluation. Under ether anaesthesia, sterile air was injected under the dorsal skin of the mice to form a sac. A sterile physiological solution or an irritant was injected into the sac thus obtained. The said irritant may be carrageen or IL-1. The mice were sacrificed by asphyxia with $CO_2$. The exudate which had developed was collected and used for the leucocyte count and for measurement of the mediators produced.

What is claimed is:

1. A method of treating a disorder characterized by production of MCP-1 protein, comprising administering to a subject an effective amount of a compound represented by the formula:

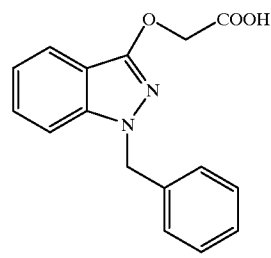

or a salt thereof with a pharmaceutically acceptable organic or inorganic base.

2. The method of claim 1, wherein the disorder is selected from the group consisting of atherosclerosis, vasculitis, interstitial lung disorders, renal disorders, postoperative complications in cardiovascular surgery, postoperative complications in transplants or organ or tissue replacements, and postoperative complications following implantation of prosthetic implants.

3. The method of claim 1, wherein the disorder is selected from the group consisting of atherosclerosis, vasculitis, interstitial lung disorders, and renal disorders.

4. The method of claim 1, wherein the subject is a human.

* * * * *